(12) United States Patent
Jensen et al.

(10) Patent No.: US 7,955,388 B2
(45) Date of Patent: Jun. 7, 2011

(54) ORTHOPEDIC CONNECTOR SYSTEM

(75) Inventors: David G. Jensen, Hillsboro, OR (US); Steven P. Horst, Dayton, OR (US)

(73) Assignee: Acumed LLC, Hillsboro, OR (US)

( * ) Notice: Subject to any disclaimer, the term of this patent is extended or adjusted under 35 U.S.C. 154(b) by 161 days.

(21) Appl. No.: 11/929,026

(22) Filed: Oct. 30, 2007

(65) Prior Publication Data
US 2008/0177291 A1    Jul. 24, 2008

Related U.S. Application Data

(60) Provisional application No. 60/856,128, filed on Nov. 1, 2006.

(51) Int. Cl.
*A61F 2/08* (2006.01)
*A61B 17/04* (2006.01)
*A61F 2/42* (2006.01)

(52) U.S. Cl. .................. 623/13.14; 606/323; 623/21.11

(58) Field of Classification Search ............... 623/13.11, 623/13.13, 13.15–13.16, 21.11, 21.14; 606/323, 606/300, 304, 301; 403/298, 303, 309, 314, 403/374.1–374.4
See application file for complete search history.

(56) References Cited

U.S. PATENT DOCUMENTS

| | | | |
|---|---|---|---|
| 1,258,580 A * | 3/1918 | Lassiter | 403/374.4 |
| 2,381,050 A | 8/1945 | Hardinge | |
| 3,916,451 A | 11/1975 | Buechel et al. | |
| 4,275,490 A | 6/1981 | Bivins | |
| 4,640,271 A | 2/1987 | Lower | |
| 4,750,492 A | 6/1988 | Jacobs | |
| 4,828,562 A * | 5/1989 | Kenna | 623/13.13 |
| 4,858,601 A | 8/1989 | Glisson | |
| 4,870,957 A | 10/1989 | Goble et al. | |
| 4,950,270 A | 8/1990 | Bowman et al. | |
| RE33,348 E | 9/1990 | Lower | |
| 4,955,910 A | 9/1990 | Bolesky | |
| 4,955,916 A | 9/1990 | Carignan et al. | |
| 5,108,437 A | 4/1992 | Kenna | |
| 5,151,104 A * | 9/1992 | Kenna | 606/328 |
| 5,217,462 A | 6/1993 | Asnis et al. | |
| 5,236,445 A | 8/1993 | Hayhurst et al. | |
| 5,281,422 A | 1/1994 | Badylak et al. | |
| 5,306,301 A | 4/1994 | Graf et al. | |
| 5,486,197 A | 1/1996 | Le et al. | |
| 5,489,210 A | 2/1996 | Hanosh | |
| 5,498,265 A | 3/1996 | Asnis et al. | |
| 5,645,588 A | 7/1997 | Graf et al. | |
| 5,665,089 A | 9/1997 | Dall et al. | |
| 5,707,395 A | 1/1998 | Li | |
| 5,741,259 A | 4/1998 | Chan | |

(Continued)

OTHER PUBLICATIONS

AcroPlate™ brochure, *aap* Implants, Inc., undated.

(Continued)

*Primary Examiner* — David Isabella
*Assistant Examiner* — Marcia Hoffman
(74) *Attorney, Agent, or Firm* — Kolisch Hartwell, PC

(57) ABSTRACT

System, including methods, apparatus and components thereof, and kits, for connecting to bone using an anchor element configured to be anchored in bone and having a selectively bendable hinge region. In some embodiments, the system may connect the anchor element to connective tissue, a bridge member, and/or to another anchor element by bending the hinge region while the anchor element is disposed in bone, thereby connecting bone to the connective tissue or bridge member, and/or connecting bone members.

19 Claims, 6 Drawing Sheets

U.S. PATENT DOCUMENTS

| | | |
|---|---|---|
| 5,769,894 A | 6/1998 | Ferragamo |
| 5,827,285 A | 10/1998 | Bramlet |
| 5,868,749 A | 2/1999 | Reed |
| 5,919,194 A | 7/1999 | Anderson |
| 5,935,129 A | 8/1999 | McDevitt et al. |
| 5,968,047 A | 10/1999 | Reed |
| 5,968,078 A | 10/1999 | Grotz |
| 5,984,924 A | 11/1999 | Asher et al. |
| 5,993,486 A | 11/1999 | Tomatsu |
| 6,048,344 A | 4/2000 | Schenk |
| 6,056,752 A | 5/2000 | Roger |
| 6,086,591 A | 7/2000 | Bojarski |
| 6,099,530 A | 8/2000 | Simonian et al. |
| 6,099,571 A | 8/2000 | Knapp |
| 6,117,160 A | 9/2000 | Bonutti |
| 6,187,008 B1 | 2/2001 | Hamman |
| 6,250,256 B1 | 6/2001 | Lin |
| 6,267,765 B1 | 7/2001 | Taylor et al. |
| 6,302,886 B1 | 10/2001 | McDevitt et al. |
| 6,319,271 B1 | 11/2001 | Schwartz et al. |
| 6,348,053 B1 | 2/2002 | Cachia |
| 6,368,326 B1 * | 4/2002 | Dakin et al. ............... 606/103 |
| 6,375,684 B1 | 4/2002 | Kriek |
| 6,413,260 B1 | 7/2002 | Berrevoets et al. |
| 6,458,134 B1 | 10/2002 | Songer et al. |
| 6,497,726 B1 | 12/2002 | Carter et al. |
| 6,508,830 B2 | 1/2003 | Steiner |
| 6,517,578 B2 | 2/2003 | Hein |
| 6,524,314 B1 | 2/2003 | Dean et al. |
| 6,533,802 B2 | 3/2003 | Bojarski et al. |
| 6,562,071 B2 | 5/2003 | Jarvinen |
| 6,575,976 B2 | 6/2003 | Grafton |
| 6,632,224 B2 | 10/2003 | Cachia et al. |
| 6,685,742 B1 * | 2/2004 | Jackson .................. 623/17.11 |
| 6,689,169 B2 | 2/2004 | Harris |
| 6,790,208 B2 | 9/2004 | Oribe et al. |
| 6,916,321 B2 | 7/2005 | TenHuisen et al. |
| 6,918,912 B2 | 7/2005 | Seemann |
| 6,942,666 B2 | 9/2005 | Overtaker et al. |
| 7,367,978 B2 * | 5/2008 | Drewry et al. ............... 606/279 |
| 2001/0051807 A1 | 12/2001 | Grafton |
| 2002/0116013 A1 | 8/2002 | Gleason et al. |
| 2002/0116066 A1 * | 8/2002 | Chauvin et al. ........... 623/17.16 |
| 2002/0161439 A1 | 10/2002 | Strobel et al. |
| 2002/0165611 A1 | 11/2002 | Enzerink et al. |
| 2002/0198527 A1 | 12/2002 | Muckter |
| 2003/0032960 A1 | 2/2003 | Dudasik |
| 2003/0088272 A1 | 5/2003 | Smith |
| 2003/0153921 A1 | 8/2003 | Stewart et al. |
| 2003/0233095 A1 | 12/2003 | Urbanski et al. |
| 2004/0015172 A1 | 1/2004 | Biedermann et al. |
| 2004/0068262 A1 | 4/2004 | Lemos et al. |
| 2004/0172031 A1 | 9/2004 | Rubecamp et al. |
| 2004/0210227 A1 | 10/2004 | Trail et al. |
| 2004/0260344 A1 | 12/2004 | Lyons et al. |
| 2005/0027294 A1 | 2/2005 | Woll |
| 2005/0113927 A1 | 5/2005 | Malek |
| 2005/0113929 A1 | 5/2005 | Cragg et al. |
| 2005/0149191 A1 | 7/2005 | Cragg et al. |
| 2005/0177167 A1 | 8/2005 | Muckter |
| 2006/0052783 A1 | 3/2006 | Dant et al. |
| 2006/0155297 A1 | 7/2006 | Ainsworth et al. |
| 2006/0235414 A1 | 10/2006 | Lim et al. |
| 2006/0271054 A1 | 11/2006 | Sucec et al. |
| 2008/0114400 A1 | 5/2008 | Dant et al. |

OTHER PUBLICATIONS

Copenheaver, Blaine R., Authorized officer, International Searching Authority, International Search Report, International Patent Application Serial No. PCT/US2007/023122; search date: May 6, 2008.

Copenheaver, Blaine, Authorized officer, International Searching Authority, Written Opinion of the International Searching Authority, International Patent Application Serial No. PCT/US2007/023122; completion date: May 6, 2008.

Rockwood A/C Screw (Design Rationale and Surgical Technique) brochure/flyer, DePuy Orthopaedics, Inc., 2001.

* cited by examiner

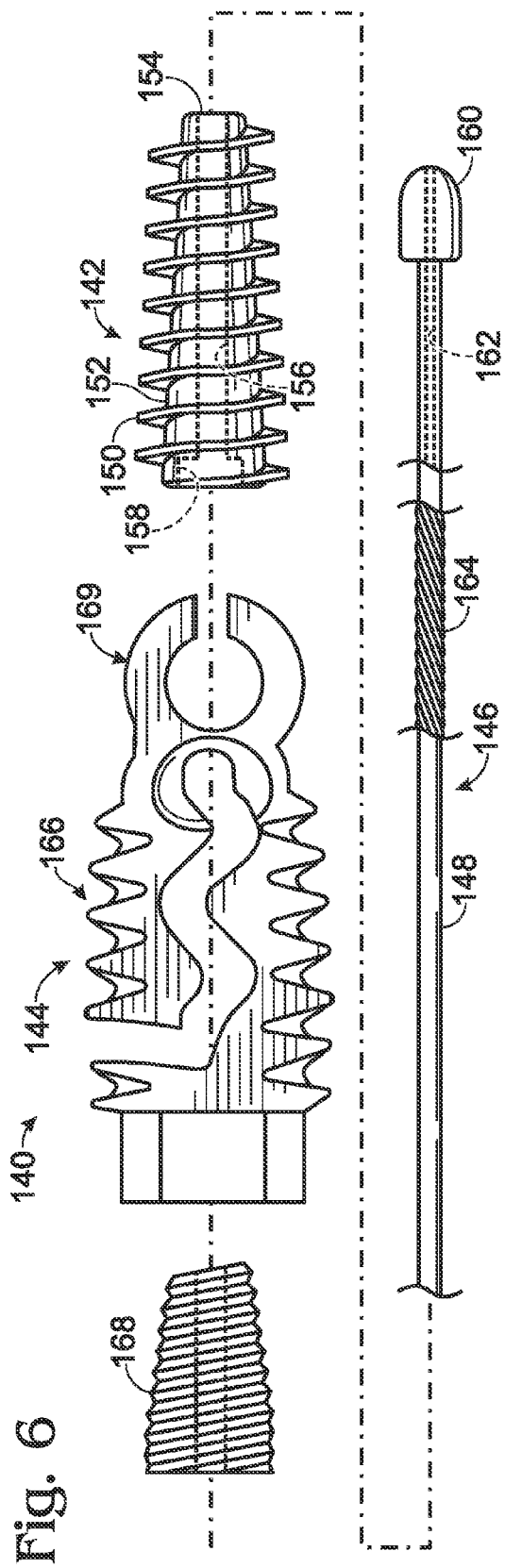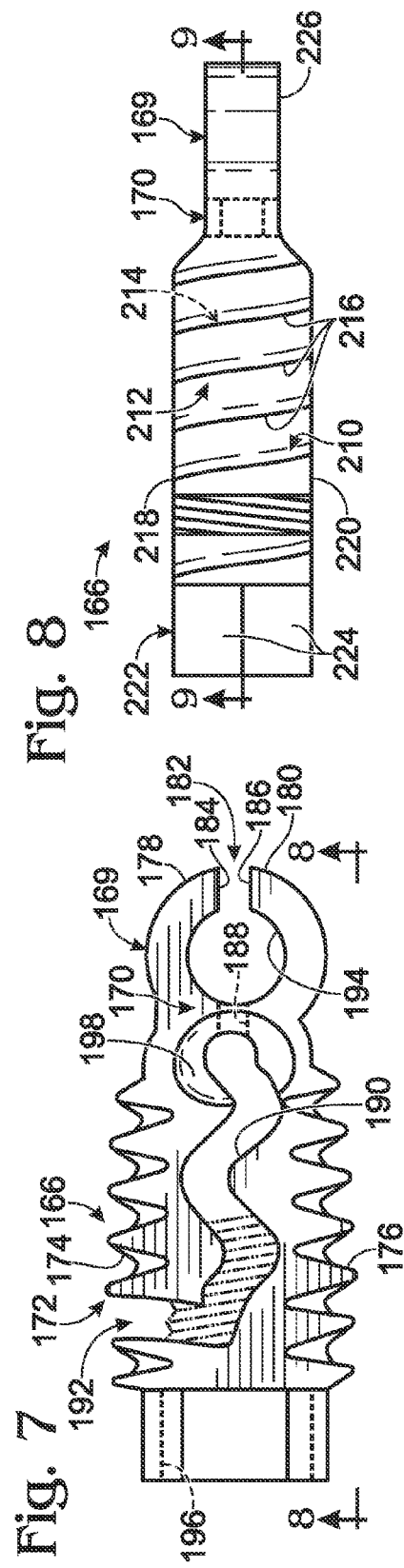

ORTHOPEDIC CONNECTOR SYSTEM

CROSS-REFERENCE TO PRIORITY APPLICATION

This application is based upon and claims the benefit under 35 U.S.C. §119(e) of U.S. Provisional Patent Application Ser. No. 60/856,128, filed Nov. 1, 2006, which is incorporated herein by reference in its entirety for all purposes.

INTRODUCTION

The skeletal portion of the human wrist, shown in FIG. 1, includes eight carpal bones 40. The carpal bones are disposed in a transverse proximal row 42 and a distal row 44 composed of four bones each. These rows provide a transition between the two bones of the forearm (radius 46 and ulna 48) and the five metacarpals 50 of the hand. The proximal row includes a scaphoid bone 52 and a lunate bone 54, among others. These bones articulate with one another (through a scapholunate joint 56), and also articulate proximally with radius 46 (through a radiocarpal joint), and distally with distal row 44 of the carpal bones.

Trauma to the wrist can produce scapholunate instability by injuring a ligament, the scapholunate interosseous ligament (SLIL) 58, that connects the scaphoid and lunate bones. The SLIL normally restricts the size of the scapholunate interval (the spacing) between the scaphoid and lunate bones and permits some limited relative rotation (about twenty degrees) of these bones about a nonfixed transverse axis extending through these bones. Injury to the SLIL can lead to arthritic degeneration of the radiocarpal joint and loss of wrist movement.

Chronic scapholunate instability may be treated with a screw, termed a Herbert screw 60. The Herbert screw, when installed, extends across the scapholunate joint and threads into both the scaphoid and lunate bones using spaced threads of the screw. The Herbert screw may fix the scaphoid and lunate bones in position until threaded engagement of the Herbert screw with bone loosens enough over time to permit relative pivotal movement of the scaphoid and lunate bones about the screw's long axis. The Herbert screw thus restricts separation (i.e., relative translational motion) of the scaphoid and lunate bones both before and after pivotal movement of these bones is permitted by this screw.

Despite its common use for treatment of scapholunate instability, the Herbert screw may have a number of disadvantages. For example, the Herbert screw may not permit relative bone movement for approximately six weeks after installation, a time period sufficient to result in formation of scar tissue and thus long term loss of wrist function. In addition, when engagement of the Herbert screw with bone loosens, bone movement generally is restricted substantially to pivotal motion about a single axis defined by the screw. The scapholunate joint thus cannot achieve its full anatomical range of articulation, and may be even more limited if the Herbert screw is installed at an unsuitable angle.

A number of other approaches also have been employed, alone or in combination, to treat scapholunate instability. These approaches may include percutaneous pinning, direct repair of the SLIL, dorsal capsulodesis, brunelli tenodesis, and SLIL reconstruction. However, each of these approaches may be unsatisfactory for various reasons.

SUMMARY

The present teachings provide a system, including methods, apparatus and components thereof, and kits, for connecting to bone using an anchor element configured to be anchored in bone and having a selectively bendable hinge region. In some embodiments, the system may connect the anchor element to connective tissue, a bridge member, and/or to another anchor element by bending the hinge region while the anchor element is disposed in bone, thereby connecting bone to the connective tissue or bridge member, and/or connecting bone members.

BRIEF DESCRIPTION OF THE DRAWINGS

FIG. 6 is an exploded view of the connector device of FIG. 5.

FIG. 7 is a side elevation view of a body portion of the bendable anchor element of FIG. 5.

FIG. 8 is a bottom view of the body portion of FIG. 7, taken generally along line 8-8 of FIG. 7.

DETAILED DESCRIPTION

Figure 1:
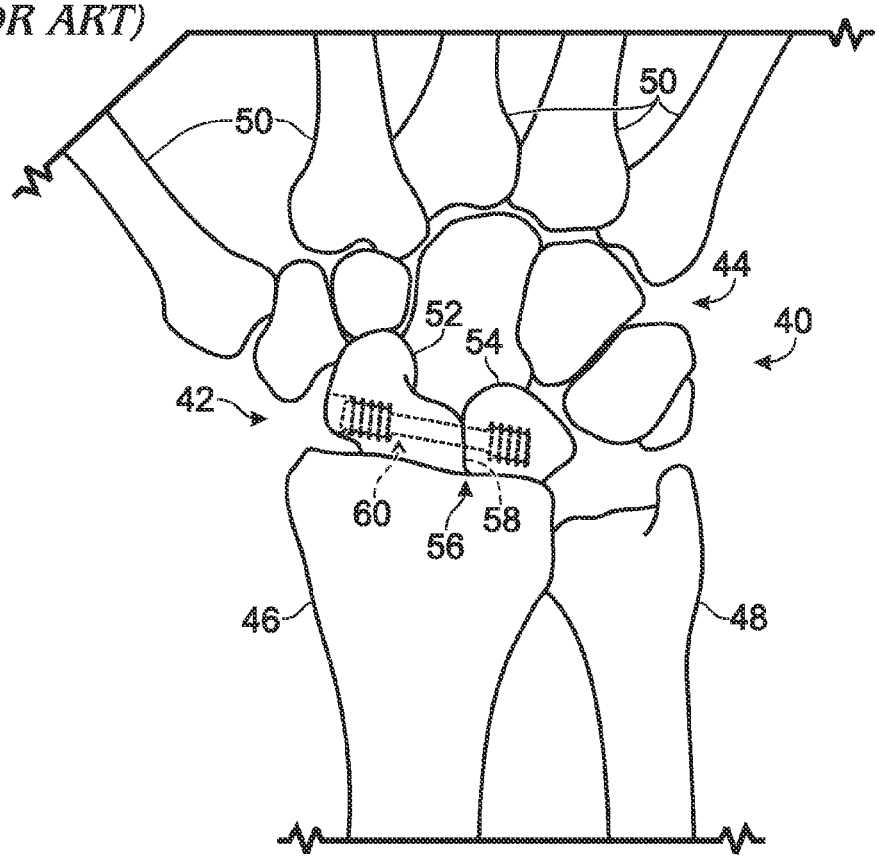
FIG. 1 is a dorsal view of the bones of the right wrist with a Herbert screw installed in and extending between the scaphoid and lunate bones of the wrist.

The present teachings provide a system, including methods, apparatus and components thereof, and kits, for connecting to bone using an anchor element configured to be anchored in bone and having a selectively bendable hinge region. In some embodiments, the system may connect the anchor element to connective tissue, a bridge member, and/or to another anchor element by bending the anchor element at the hinge region while the anchor element is disposed in bone, thereby connecting bone to the connective tissue or bridge member, and/or connecting bone members.

The (bendable) anchor element may include a clamp, an actuation element, and/or bone-engagement structure, among others.

The clamp may have opposing portions or jaws (including, e.g., two or more jaw elements) with a spacing responsive to changes in the shape of the bendable anchor element. The jaws or other gripping structure may be included in a body (e.g., a monolithic body) of the anchor element. The body may define legs that operate the jaws through a hinge region of the body. More particularly, each leg may have a corresponding jaw element opposing the leg across the hinge region and rigidly coupled to the leg. Accordingly, the leg and its corresponding jaw element may pivot about the hinge region when the body of the bendable anchor element is bent selectively at the hinge region, such that urging the legs apart also urges the jaws together (e.g., radially inward) and/or generally toward one another.

The actuation element may assemble with the body of the bendable anchor element. For example, the body may define an opening for receiving the actuation element. The opening may extend generally along the body, such as at least substantially parallel to the central axis (and/or long axis) of the body. In some embodiments, the opening may have an internal thread for receiving an actuation element (such as a jackscrew) having an external thread. Furthermore, the opening may taper toward the jaws (and/or the actuation element may taper towards its leading end) such that advancement of the actuation element expands a portion of the body, defined by the legs, by wedging the legs apart. The bendable anchor element thus may be anchored in bone (or may be anchored in bone more securely) by deformation (via bending) after placement into bone, and/or may include one or more projections that engage bone as the anchor element is advanced into bone.

The bendable anchor element may be paired with a bridge member and/or another (e.g., non-bendable) partner anchor element, to provide a connector device. The connector device may be used for securing the bridge member to bone via the bendable anchor element and/or for connecting bone members via the pair of anchor elements. The connector device thus may be configured to be placed in and anchored to respective bone members, such as distinct bones and/or fragments of the same bone. In some embodiments, the anchor elements may be coupled to one another via a bridge member extending between the anchor elements and into and/or through the jaws of the bendable anchor element. The bridge member may be a separate component (e.g., a flexible wire) coupled fixedly or movably to the body of the partner anchor element, or the bridge member and the partner anchor element may be part of the same monolithic structure (i.e., formed as one piece). The bridge member may be gripped by the jaws when the clamp is actuated (i.e., the bendable anchor element is bent), to connect the pair of anchor elements after their placement into the respective bone members, with a suitable spacing between the anchor elements. Accordingly, the bridge member may offer relative movement of the pair of anchor elements and their respective bone members. The relative movement may be via flexion of the bridge member itself and/or via relative pivotal (e.g., twisting) and/or translational motion of the bridge member relative to the partner anchor element. The connector device and methods of connecting bones with the connector device thus may provide better control over the spacing and/or range of permitted movement between connected bones, thereby offering an improved approach to treating scapholunate instability.

Figure 2:
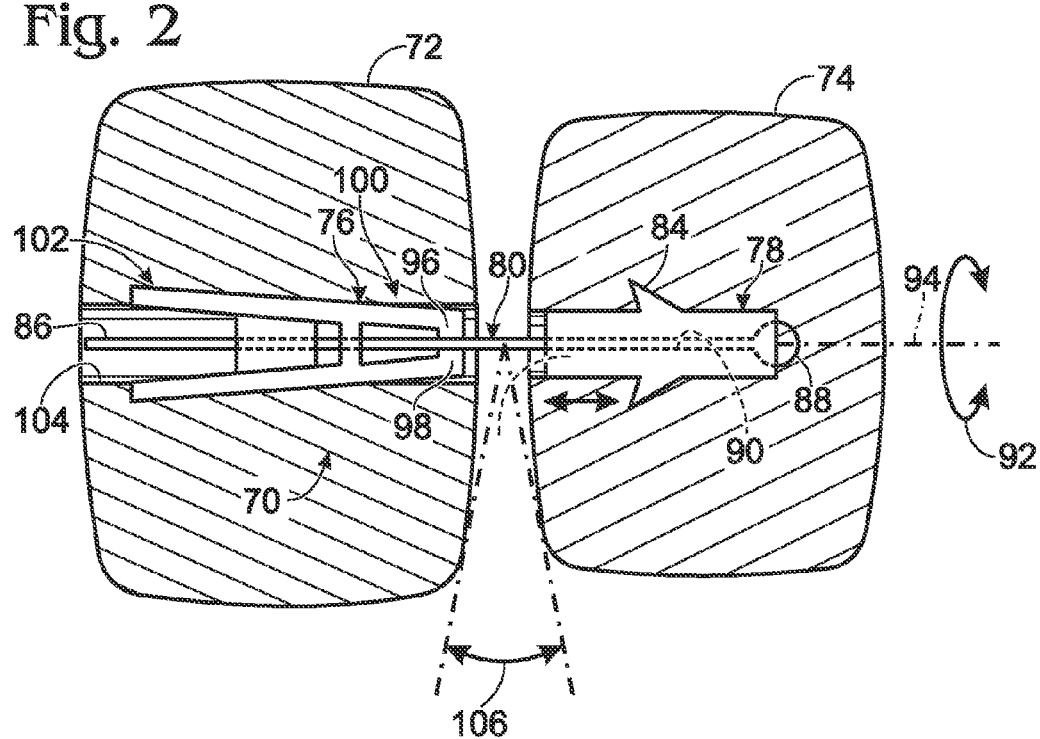
FIG. 2 is a somewhat schematic view of an exemplary connector device installed in and connecting a pair of bone members, with the connector device including a bendable anchor element and a bridge member gripped by the bendable anchor element after the anchor element has been bent, in accordance with aspects of the present teachings.

FIG. 2 shows an exemplary connector device 70 for connecting bone members 72, 74. The connector device may include a pair of anchor elements, namely, a bendable anchor element, deformable anchor 76, and a partner anchor element, partner anchor 78, connected by a bridge member 80 (also termed a bridge portion of the connector device). The bridge member may be gripped by the deformable anchor, when the deformable anchor is bent after the anchor elements have been placed into bone, thereby connecting the bridge member to bone member 72 and/or connecting bone members 72 and 74 to one another. In some embodiments, partner anchor 78 may be omitted from the connector device.

Partner anchor 78 may be structured to be disposed in and anchored to bone. Accordingly, the partner anchor may include one or more projections 84 (e.g., ribs, barbs, and/or an external thread, among others) that hold the partner anchor in place relative to bone member 74, during and/or after placement of the partner anchor into the bone member.

Bridge member 80 may be structured for creating a connection (a bridge) between the anchor elements and/or between deformable anchor 76 and any other suitable engineered (manufactured) component and/or anatomical structure. Bridge member 80 thus may be connected to partner anchor 78 and may extend from the partner anchor into and/or through deformable anchor 76 and bone member 72. Partner anchor 78 and bridge member 80 may be part of the same unitary and/or monolithic structure or these portions, as shown here, may be provided by discrete components that are coupled movably. Bridge member 80 may include an elongate stem 86 connected fixedly or movably (e.g., pivotably) to a head 88. Stem 86 may extend through a longitudinal passage (e.g., an axial bore or cannulation) 90 defined by partner anchor 78. Head 88 may be sized larger than the passage so that the head cannot be pulled through the partner anchor, to restrict separation of the bridge member from the partner anchor. However, the head may be shaped to permit relative pivotal motion, indicated at 92, of the bridge member and partner anchor about a long axis 94 defined by stem 86 and/or passage 90.

Deformable anchor 76 may be structured to include (two or more) jaws 96, 98 that receive at least or only a section of stem 86 of the bridge member. The jaws may be included in a clamp 100 (or other gripping structure) that can be actuated, with the deformable fastener in bone, such that jaws 96, 98 grip at least or only a section of stem 86. (The clamp is shown here in an actuated configuration.) Actuation of the clamp may be performed by bending the deformable anchor, such as by urging a portion (or opposing portions) of the deformable anchor outward, indicated at 102, into adjacent bone. Accordingly, clamp actuation may be performed after the deformable anchor has been placed into a hole 104 formed in bone member 72, such that the deformable anchor engages a wall of the hole, to anchor (and/or to more securely fix) the deformable anchor in bone member 72.

Connector device 70 may be structured to permit any suitable relative motions of the anchor elements (and/or associated bone members). For example, the bone members may be permitted to pivot about axis 94 relative to one another. In addition, the bone members may be permitted to pivot about a transverse axis (or axes) extending transversely through stem 86, via flexion of the stem, indicated at 106, at one or more positions (or a continuous range of positions) disposed generally between the anchor elements. Accordingly, the angular disposition of pivot axis 94 relative to bone member 72 may be adjusted dynamically by this flexion. Furthermore, in some embodiments, the bone members may be permitted to move translationally relative to one another to adjust the spacing between the bone members. In particular, head 88 of the bridge member may move deeper into bone member 74 (rightward in the current view) if a suitable cavity is present in the bone member past partner anchor 78, and/or head 88 may move translationally along a wider region of passage 90 sized to receive the head.

Figure 3:
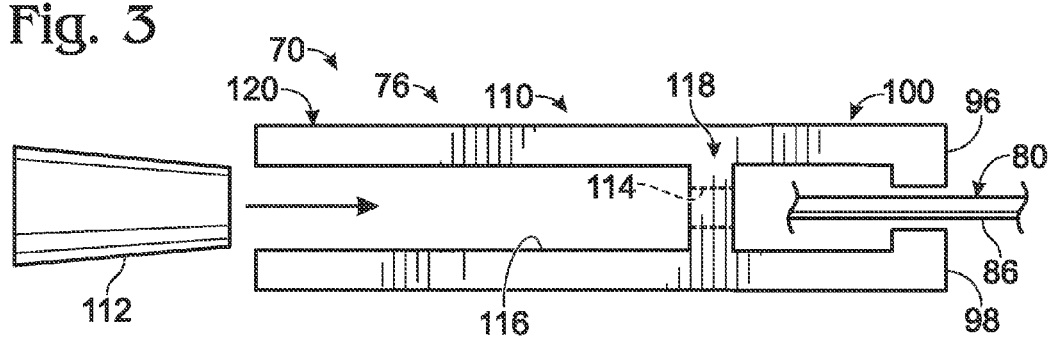
FIG. 3 is a fragmentary, side elevation view of selected aspects of the connector device of FIG. 2, particularly the anchor element and the bridge member received by jaws of the anchor element, in the absence of bone and prior to bending the anchor element, in accordance with aspects of the present teachings.

FIG. 3 shows selected aspects of connector device 70, particularly deformable anchor 76 and an associated section of stem 86 of bridge member 80. The deformable anchor may include a body component 110 and an actuation element 112 configured to engage and controllably deform the body component. Here, the actuation element is not yet assembled with body component 110, and stem 86 of the bridge member extends into and through jaws 96, 98 of the body component prior to actuation of clamp 100. Accordingly, jaw elements 96, 98 of the clamp may be spaced from the stem to permit the body component of the deformable anchor to slide along the stem (and/or to pivot about the long axis of the stem). The stem of the bridge member may extend into body component 110 but not through the body component. Alternatively, or in addition, the body component may define one or more openings 114, 116 that permit the stem to extend at least mostly or completely through the body component.

Body component 110 may be structured for regional expansion and contraction during deformation. For example, the body component may include a hinge region 118 defined by a web at which the body component is bent selectively, to define a distal contraction region that includes the clamp, and a proximal expansion region 120 that engages bone and actuation element 112.

Figure 4:
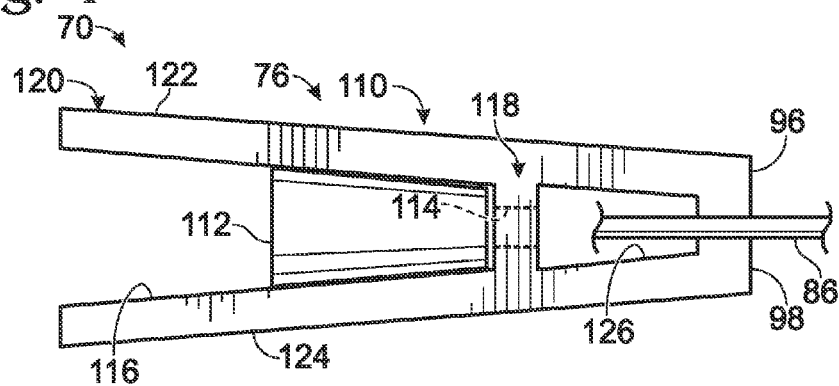
FIG. 4 is a fragmentary, side elevation view of the connector device of FIG. 2, taken generally as in FIG. 3 after the anchor element has been bent such that the anchor element grips the bridge member to create a connection between bone and the bridge member, in accordance with aspects of the present teachings.

FIG. 4 shows connector device 70 generally as in FIG. 3, but after deformation of deformable anchor 76 such that the pair of anchor elements (see FIG. 3) are coupled to one another. In particular, actuation element 112 may be advanced along opening 116 of body component 110, to urge legs 122, 124 of expansion region 120 apart and to urge jaw elements 96, 98 toward one another such that the jaws grip stem 86 of the bridge member. Actuation element 112 (and/or opening 116) may be tapered to promote a wedging action during advancement of the actuation element. The wedging action may change the relative angular disposition of regions of the body component (e.g., the legs of the body component), using the web of the hinge region as a pivot site at which bending is focused. Furthermore, opening 116 and a clamp opening 126 that partially defines jaws 96, 98 may be transverse through-openings that extend completely through the body component, for example, along parallel transverse axes of the body component, to facilitate bending the body component at hinge region 118.

Further aspects of the present teachings are described in the following sections: (I) anchor elements, (II) bridge members, (III) composition of connector devices, (IV) methods of installing connector devices, (V) kits, and (VI) examples.

I. Anchor Elements

The connector devices of the present teachings each may include one or more anchor elements, also termed anchors. An "anchor element," as used herein, refers to any fastener device configured to be secured to bone such that translational and/or pivotal movement of the fastener device is restricted relative to bone. Generally, the anchor element is secured by engagement between the anchor element and bone such that the anchor element cannot be readily pushed or pulled out of position. However, in some embodiments, the anchor element may be turned readily while anchored, particularly with the aid of a tool such as a driver.

An anchor element may be configured to be anchored in bone. The anchor element thus may be sized and shaped for placement into bone, such as placement at least mostly or completely within a bone(s). Furthermore, the anchor element may be shaped for anchoring engagement with bone during and/or after placement into the bone. Anchoring engagement may be provided by any suitable projection(s) disposed on or near an outer surface of the anchor element. Exemplary projections may extend along a path that is helical, circular, linear, arcuate, angular, non-elongate, and/or the like. Accordingly, the projections may include an external thread(s), a rib(s), a barb(s), a prong(s), etc. The projections may be formed on a central body portion of the anchor element and may be fixed or movable relative to the central body portion and/or relative to one another. For example, the anchor element may include one or more biased projections that bend or deform against their bias as the anchor element is placed into bone and then engage bone to hold the anchor element in position via the bias. In some embodiments, the anchor element may be secured to bone alternatively, or in addition, using an adhesive.

An anchor element may have any suitable number of components. For example, the anchor element may be formed unitarily, such as in a monolithic structure or with two or more pieces/components fixed to one another. Alternatively, the anchor element may have two or more discrete components that are connected or connectable to one another in a movable relationship. Exemplary anchor elements with two or more components may include a deformable body component and an actuation component that assembles with the deformable body component (e.g., see Example 1), a deformable (or non-deformable) body with a pair of body components connected via a fixed or movable joint, and/or the like.

An anchor element may have any suitable shape. For example, the anchor element may have a central body portion with a linear, angular, and/or arcuate profile created by a uniform or nonuniform diameter. The central body portion thus may taper linearly or nonlinearly toward a leading and/or trailing end of the anchor element, and may be cylindrical, frustoconical, conical, ellipsoidal, frustoellipsoidal, or the like. One or both ends of the anchor element may be flat (planar), rounded, or pointed, among others. Furthermore, the anchor element may define concave surface structure (e.g., a socket) or convex surface structure (e.g., a head) for receiving a driver that advances the anchor element translationally and/or by turning the anchor element, among others.

An anchor element may be structured as a bone screw. The term "bone screw," as used herein, refers to any bone fastener having an external thread, particularly an external thread formed on a shank of a bone fastener. The bone screw may have a head and a shank or may lack a distinct head. The external thread may be a continuous rib or may be interrupted such that the external thread is composed of two or more discrete thread segments. In addition, the external thread may generally helical, with a uniform or varying thread pitch. Furthermore, the external thread may be a single (continuous or interrupted) thread, extending along only one helical or generally helical path, or the bone screw may have two or more distinct external threats extending along two or more non-intersecting helical or generally helical paths, to provide a multi-threaded structure. The bone screw also may have structure for drilling into bone (a self-drilling bone screw) and/or for forming a thread in bone (a self-tapping bone screw).

A connector device may include one, two (a pair), or more anchor elements. If the connector device includes a pair of anchor elements, each member of the pair may be a bendable anchor element or a substantially non-bendable anchor element.

The pair of anchor elements may have the same or different shapes. If of the same shape, both anchor elements (and/or body portions thereof) may, for example, be cylindrical or both may be frustoconical, among others. If of different shapes, one of the anchor elements may, for example, have a frustoconical shape and the other anchor element of the pair may have a cylindrical shape, among others. In addition, the anchor elements of the pair may have similar or different engagement structures for anchoring each anchor element in bone. For example, both of the anchor elements may have an external thread, one of the anchor elements may have an external thread and the other may be nonthreaded externally, or both of the anchor elements may be externally non-threaded.

The pair of anchor elements may have the same size or different sizes. For example, the anchor elements may have the same length or may have different lengths, such as a leading (and/or non-bendable) anchor element that is shorter (or longer) than a trailing (and/or bendable) anchor element. In addition, the anchor elements may have the same or different diameters, such as a leading (and/or non-bendable) anchor element that is narrower (or wider) than a trailing (and/or bendable) anchor element.

Further aspects of anchor elements that may be suitable for the connector devices are described elsewhere in the present teachings, such as near the beginning of the Detailed Description and in Example VI, among others.

II. Bridge Members

The connector devices of the present teachings each may include one or more bridge members. A "bridge member," as used herein, refers to any portion of a connector device that connects an anchor element to another portion of the connector device (e.g., another anchor element) and/or to an anatomical structure (e.g., bone, cartilage, ligament, etc.). The bridge member and an anchor element may be part of the same monolithic structure, may be part of the same unitary structure, or may be separate components that are movably connected/connectable to each other.

The bridge member may have any suitable shape. In exemplary embodiments, the bridge member is elongate, e.g., with a length that is at least about two, five, ten, or more times as great as its diameter. The bridge member may have any suitable length, such as a length that is less than, at least about as great as, or substantially greater than the length of one anchor element or a combined length of a pair of (or all) anchor elements, among others. The bridge member (and/or a stem portion thereof) also may have any suitable diameter, such as a diameter that is substantially less than, about the same as, or substantially greater than the diameter of one or more anchor elements of a corresponding connector device. In exemplary embodiments, the bridge member has a stem portion that is lesser in diameter than a cannulation extending through one or more of the anchor elements, and a head portion that is greater in diameter than the cannulation. The bridge member (and/or a stem portion thereof) may have a substantially uniform diameter or the diameter may vary along the length of the bridge member (and/or stem portion). For example, the bridge member may taper toward one or both ends or may be undulated (or vary in diameter stepwise) along its length. Furthermore, the bridge member may be solid or hollow along a portion or all of its length.

The bridge member may have any suitable mechanical properties. For example, the bridge member may be rigid or flexible. If flexible, the bridge member may be (1) flexible resiliently (i.e., elastic) such that the bridge member is biased toward its original shape (e.g., unbent), (2) flexible nonresiliently (e.g., malleable) but rigid enough to hold its shape, or (3) may be flaccid (limp), among others. Suitable bridge members may include wires, lines (e.g., thread (such as a suture), string, cord, etc.), and/or the like.

Further aspects of bridge members that may be suitable for connector devices are described elsewhere in the present teachings, such as near the beginning of the Detailed Description and in Example VI, among others.

III. Composition of Connector Devices

Each component of a connector device (e.g., a deformable anchor, an actuation element, a (nondeformable) partner anchor, and/or a bridge member (e.g., a head and/or stem thereof)) may be formed of any suitable biocompatible and/or bioresorbable material(s). Exemplary biocompatible materials include (1) metals (for example, titanium or titanium alloys, alloys with cobalt and chromium (cobalt-chrome), stainless steel, etc.); (2) plastics (for example, ultra-high molecular weight polyethylene (UHMWPE), polymethylmethacrylate (PMMA), polytetrafluoroethylene (PTFE), polyetheretherketone (PEEK), nylon, polypropylene, and/or PMMA/polyhydroxyethylmethacrylate (PHEMA)); (3) ceramics (for example, alumina, beryllia, calcium phosphate, and/or zirconia, among others); (4) composites; (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, and/or natural polymers (such as collagen or other polypeptides, polysaccharides (e.g., starch, cellulose, and/or chitosan), any copolymers thereof, etc.); (6) bone tissue (e.g., bone powder and/or bone fragments); and/or the like. In some examples, these materials may form the core of an anchor element and/or a bridge member and/or a coating thereon.

The components of a connector device may be formed of the same material(s) or different materials. Exemplary configurations with different materials may include (1) an anchor (s) formed of metal and a bridge member that is not metal, or (2) a deformable anchor, a bridge member, and/or partner anchor formed of different metals, such as a bridge member formed of a more flexible, malleable, and/or elastic metal and one or both anchors formed of a less flexible, malleable, and/or elastic metal. In some embodiments, the bridge member (and/or a stem portion thereof) may be substantially more elastic than the anchor(s), for example, with the bridge member formed by or including a very elastic metal alloy, such as a shape memory alloy (e.g., a "superelastic" alloy formed of titanium and nickel such as NiTinol).

IV. Methods of Installing Connector Devices

The connector devices of the present teachings may be installed in bone by any suitable methods. Exemplary steps that may be performed in the methods are listed below. These steps may be performed in any suitable order, in any suitable combination, and any suitable number of times.

At least one bone member may be selected for receiving a connector device. The bone member may be an intact bone(s) or may be one or more fragments of a bone produced by breaking or cutting the bone, among others. Exemplary bones for receiving a connector device may include one or more bones of the hand/wrist (carpals, metacarpals, and/or phalanges), arms (radius, ulna, and/or humerus), legs (femur, tibia, fibula, and/or patella), ribs, vertebrae, scapulas, pelvic bones, cranial bones, and/or the mandible, among others. In some examples, two or more bone members may be selected for receiving a connector device. The two or more bone members may correspond to different bones or distinct fragments of the same bone, among others. The bone members may be adjacent one another naturally or may be moved so that they are adjacent one another. The bone members may have sustained or be associated with any suitable injury. For example, the bone members may result from an injury to bone (such as a fracture and/or an osteotomy, among others) or may be adjacent and/or connected to injured soft/connective tissue (e.g., ligament, tendon, and/or muscle, among others). In some examples, the bone members may be bones that articulate with one another through an anatomical joint. Any suitable anatomical joints may be selected to be spanned by a connector device, including the scapholunate joint, the acromioclavicular joint, etc.

In some embodiments, connective tissue may be selected for connection to the bone member. The connective tissue may, for example, be orthopedic connective tissue, namely, tendon, ligament, and/or muscle, and may be a band of connective tissue. The band of connective tissue selected may have a size (e.g., width, diameter, and/or thickness) such that a section of the band can be received by a gripping structure and/or jaws of a deformable anchor. Accordingly, in some cases, the methods may involve creating a connection between a band of connective tissue and a bone member using only a deformable anchor (and not a bridge member or another anchor).

A connector device for installation may be selected. The connector device may have any suitable combination of the features described elsewhere in the present teachings. For example, the connector device may include a deformable anchor and a bridge member; a deformable anchor, a (deformable or nondeformable) partner anchor, and a bridge member; and/or a deformable anchor and a partner anchor, with the partner anchor including an integral bridge portion; among others. The connector device may have a size (e.g., length and width) selected according to the size of the bone member(s) into which the connector device is to be placed (e.g., a narrower and/or shorter connector device for smaller bone members and a wider and/or longer connector device for larger bone members).

Each anchor element of the connector device may be disposed in a cavity of a respective bone member. Disposing the anchor elements may include advancing a leading anchor element first through a more proximal (closer and/or more accessible) of the bone members and then into a more distal (spaced and/or less accessible) of the bone members. The leading anchor element may be placed in its respective bone member at about the same time as a bridge member of the connector device, or the bridge member may be placed in the bone member before (or after) the leading anchor element. The leading anchor element may be nondeformable or deformable. In some examples, placement of a leading anchor element into bone may be omitted from the methods, such that only a single anchor element is disposed in a bone member, before, at the same time as, or after placement of a bridge member into bone. In any event, a trailing anchor element also may be disposed in its respective bone member. The trailing anchor element may be deformable or nondeformable. Furthermore, the trailing anchor element may be disposed in its respective bone member after (or before) the bridge member is placed into bone.

Disposing each anchor element in its respective bone member may include anchoring the anchor element to bone. For example, the anchor element may be advanced into bone by turning the anchor element, such that the anchor element is disposed in threaded engagement with bone (anchored to bone) during the step of disposing. Alternatively, the anchor element may be advanced into bone by pushing (or pulling) the anchor element in the bone. In some examples, the anchor element may fit tightly into a cavity in bone such that forcing (e.g., pounding) the anchor element translationally into bone also anchors the anchor element in the bone. In some examples, the anchor element may not fit tightly into a cavity in bone when the anchor element is first disposed in bone. Accordingly, the anchor element may be anchored in bone after the anchor element is disposed in bone by deforming the anchor element for enhanced engagement with bone such that the anchor element has a translationally and/or pivotally fixed position in bone.

The step of disposing also may position a bridge member to extend between a pair of anchor elements and span a gap (or junction) between the anchor elements. The bridge member thus also may span a gap (or junction) between the respective bone members in which the anchor elements are disposed. Accordingly, the bridge member may extend into and/or through one or both of the anchor elements. In particular, the bridge member may extend into jaws of a deformable anchor element such that at least a section of the bridge member is disposed between the jaws.

The deformable anchor element may be bent after it is disposed in bone. Bending deforms the anchor element such that the jaws of the anchor elements engage and grip the bridge member, to restrict relative longitudinal movement of the bridge member and the deformable anchor element. Bending may be performed via a tool that engages an actuation element of the deformable anchor element and/or may be performed by direct engagement between the tool and a deformable body of the anchor element.

The connector device may be left in place indefinitely/permanently or may be removed at a later time. If left in place, a portion (e.g., an anchor element(s) and/or a bridge member) or all of the connector device may be bioresorbable such that the portion or all of the connector device is broken down and absorbed by the body over time. If removed, removal of the connector device may take place at any suitable time. Exemplary times include at a predefined time or after a predefined amount of healing.

V. Kits

The connector devices of the present teachings may be provided in kits. A kit optionally may include any suitable combination of (1) one or more deformable anchor elements of the same and/or different sizes, (2) one or more nondeformable partner anchor elements of the same and/or different sizes, (3) one or more bridge members, (4) one or more drills and/or other tools for forming cavities (holes) in bone for receiving the connector devices, (5) one or more drivers and/or other tools (such as gripping tools and/or cutting tools (e.g., a wire cutter)) for installing and/or removing the connector devices, (6) one or more guide members such as guide wires for extending into/through and guiding components of the connector devices, drills, and/or drivers, as appropriate, and/or (7) a case for holding and/or organizing other components of the kit. Components of the kit may be sterile and/or sterilizable (e.g., autoclavable). In some examples, components of the kit, such as anchor elements, bridge members, and/or guide wires, may be intended or suitable for single use. In some examples, components of the kit, such as drills and/or drivers, may be intended or suitable for repeated use.

VI. EXAMPLES

The following examples describe selected aspects and embodiments of systems for connecting bone members and/or fastening to bone. These examples are included for illustration and are not intended to limit or define the entire scope of the present teachings.

Example 1

Exemplary Device for Connecting Bone Members

This example describes an exemplary connector device 140 for connecting bone members; see FIGS. 5-13.

Figure 5:
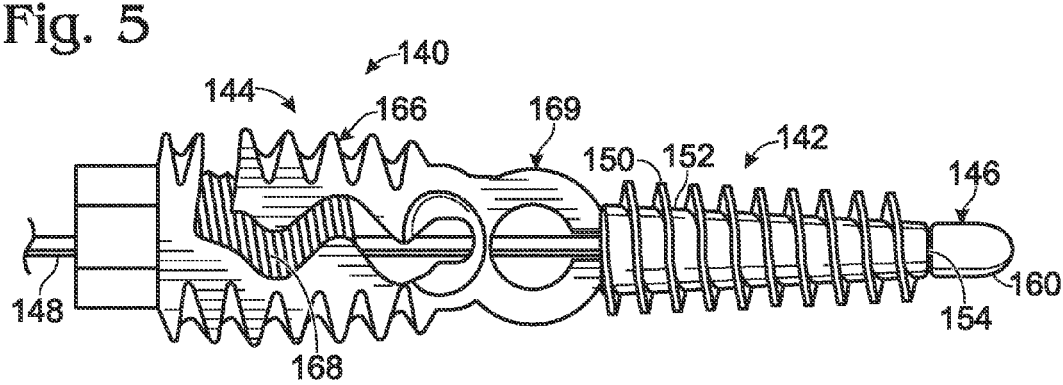
FIG. 5 is a side elevation view of another exemplary connector device for connecting bone members and including a pair of anchor elements coupled by bending one of the anchor elements ("a bendable anchor element") after the anchor elements have been placed into their respective bone members, in accordance with aspects of present teachings.

FIGS. 5 and 6 show connector device 140 in respective assembled and exploded configurations, in the absence of bone. Connector device 140 may include a pair of anchor elements, namely, a leading anchor 142 and a trailing anchor 144. The anchor elements may be coupled to one another via an elongate bridge member 146 that includes a wire 148, also termed a rod, for spanning a junction or gap between the anchor elements. The elongate bridge member may be a discrete, separable component, as shown here, or may be unitary and/or monolithic with leading anchor 142.

Leading anchor 142 may be structured to be anchored in bone. The leading anchor thus may have an external thread 150 formed on a cylindrical and/or tapered body 152. Here, both external thread 150 and body 152 taper in diameter toward a leading or distal end 154 of the anchor, to provide a directionality for rotational advancement of the anchor into bone, with the distal end entering bone first. The leading anchor may be solid, for example, if the leading anchor provides a bridge portion extending proximally from the anchor, namely, toward the trailing anchor. Alternatively, the leading anchor may be cannulated, with an axial bore 156 (a cannulation) extending lengthwise through the anchor (see FIG. 6). The axial bore may be larger in diameter than wire 148 of the bridge member so that the wire can be received slidably in the axial bore. The leading anchor also may define a tool-engagement structure such as a hexagonal socket (or projection) 158, disposed proximally on the anchor, for engagement by a driver that turns the leading anchor (thereby threading the leading anchor into bone).

Bridge member 146 may be structured to couple the anchors to one another. The bridge member may include an elongate stem (e.g., wire 148) and a head 160 attached to the stem. Head 160 may be lesser in diameter than the diameter of distal end 154 of body 152 of the leading anchor such that placement of the head into bone first does not interfere with the ability then to place the leading anchor into threaded engagement with bone. Alternatively, or in addition, the head of the bridge member may include an external thread and/or a cutting edge to provide respective threaded engagement with, and/or drilling into, bone. In some embodiments, the head and/or stem of the bridge member may anchor the bridge member sufficiently enough that a discrete leading anchor may be omitted from the connector device. Furthermore, the elongate stem may have any suitable length, such as at least as long as the leading anchor, at least as long as the combined length of the leading and trailing anchors, and/or substantially longer than the combined length of the leading and trailing anchors, among others.

Bridge member 146 may be structured to be received over a guide wire or other suitable guide member. Accordingly, the bridge member may be cannulated, with an axial passage 162 (shown as fragmentary here) extending lengthwise through wire 148 and head 160 of the bridge member. Wire 148 thus may be of monofilament construction or may have a multifilament construction, such as a braided wire (analogous to a "Chinese finger trap"), with wire filaments 164 (shown as fragmentary here), twisted/interlaced about a central axis to define a stem portion of the axial passage.

Trailing anchor 144 may include a deformable body 166 and an actuation element 168 structured as a jackscrew that assembles with the deformable body. Deformable body 166 may define a clamp 169 distally (or proximally) for engagement with wire 148. Advancement of the jackscrew may bend the deformable body such that the clamp grips and/or crimps wire 148 (see below).

FIG. 7 shows a side view of deformable body 166, with the jackscrew presented in phantom outline. Deformable body 166 may define a series of openings (e.g., contiguous openings) that create clamp 169, a hinge region 170 at which the deformable body is bent selectively, and an expansion region 172 with a pair of legs 174, 176 that expand to contract/compress jaws 178, 180 of the clamp.

The openings may include a jaw opening 182 flanked by respective gripping surfaces 184, 186 of the jaws. The gripping surfaces may be generally parallel, as shown here, to increase surface contact with the bridge member upon clamp actuation, or may be nonparallel. Alternatively, or in addition, the gripping surfaces may include projections, such as ridges and or prongs (e.g., serrations), that selectively deform and/or penetrate the surface of the bridge member (and/or crimp the bridge member) upon clamp actuation to enhance engagement and/or restrict axial slippage of the bridge member.

The openings also may include an axial passage 188. The axial passage may function to receive the bridge member and restrict lateral movement of the bridge member out of alignment with deformable body 166 (particularly alignment with jaws 178, 180) prior to clamp actuation.

The openings further may include a transverse through-passage 190 that divides at least a longitudinal section of the deformable body into legs 174, 176 connected only by a web created by hinge region 170. The through-passage may extend to the hinge region from a side of the deformable anchor, indicated at 192, and/or from an end of the deformable body (e.g., see FIG. 3). Furthermore, at least a portion of the through-passage may extend generally axially along a linear, angular, and/or curved path, such as the serpentine path shown here.

The deformable body may include additional openings. For example, the deformable body may include a distal mouth region 194 disposed adjacent and proximal to jaw opening 182 and defining an inner contour of clamp 169. The deformable body further may define a proximal receiver opening 196 for receiving the bridge member and/or the actuation element. Additionally, the deformable body may include one or more recessed regions 198 disposed in and/or adjacent the hinge region, to thin and thereby weaken the hinge region for selective bending therein.

FIG. 8 shows various surface features of deformable body 166. The surface features may include a thread(s), a tool-engagement structure(s), and/or a nonuniform thickness, among others, as described below.

The deformable body may include an external thread(s) 210 formed by discrete, spaced threaded regions 212, 214 that oppose one another across the body. Each threaded region may define a plurality of thread segments 216 that are sized and positioned to correspond to segments of a generally helical path (or two or more helical paths if the external thread is multi-threaded). Threaded regions 212, 214 may be separated by opposing nonthreaded faces 218, 220 of the body, which may be flat (planar), as shown here, or nonplanar (e.g., concave and/or convex). Furthermore, opposing faces 218, 220 may be substantially parallel to one another, as shown here, or may be nonparallel. Accordingly, the deformable body may have a width, measured between threaded regions 212, 214, that is greater than the thickness of the body, measured between faces 218, 220. In other examples, the deformable body may lack nonthreaded lateral faces that interrupt an external thread. In these examples, the external thread may, in some cases, be interrupted only by a transverse through-opening that helps define the hinge region of the body.

Deformable body 166 may have a head 222 defined by a proximal end region of the anchor. Head 222 may be shaped to have facets 224 configured for engagement by a driver that turns the body during installation in bone. The facets thus may provide a hexagonal head (or other convex driver-engagement structure), or at least a substantial portion thereof. In other embodiments, the head and/or a shank may define a socket for engagement by a driver.

Deformable body 166 further may have a tail region 226 opposing the head. The tail region may be thinner than portions of the body defining the head and the external thread, to facilitate bending the body in or near the tail region. Accordingly, the tail region may include clamp 169 and hinge region 170, among others.

Figure 9:
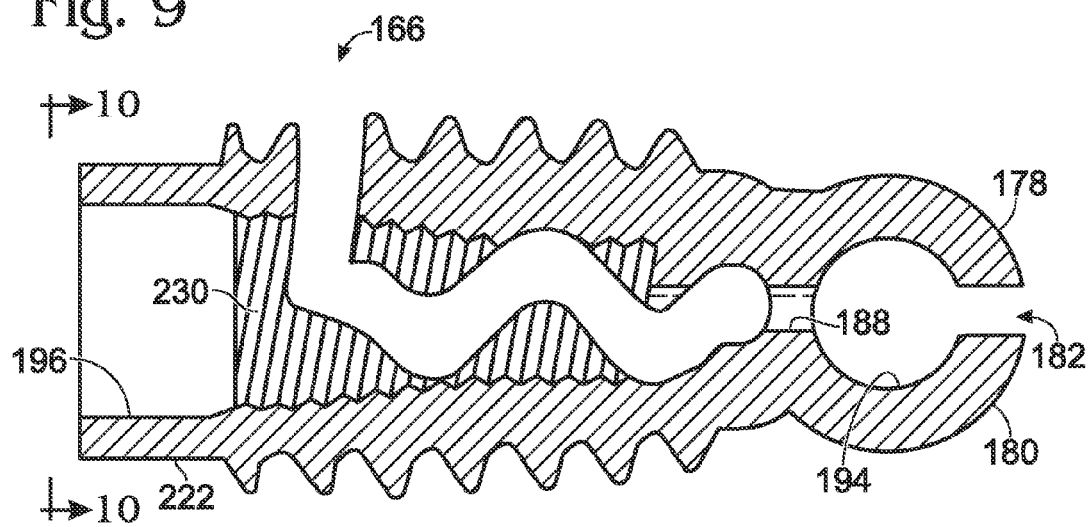
FIG. 9 is a sectional view of the body portion of FIG. 7, taken generally along line 9-9 of FIG. 8.

FIG. 9 shows a longitudinal sectional view of deformable body 166. The stem of a bridge member may be received by the body by feeding an end of the stem (1) between jaws 178, 180 through jaw opening 182, (2) through mouth region 194, (3) through axial bore 188, (4) through proximal receiver opening 196, (5) and out the head of the body. In contrast, the actuation element (see element 168 of FIG. 6) may be assembled with the body from the opposing direction by placement of the actuation element through head 222 and into threaded engagement with an internal thread 230 defined adjacent the head by receiver opening 196. The receiver opening thus may be tapered in a direction away from the head, as shown here, or may be nontapered.

Figure 10:
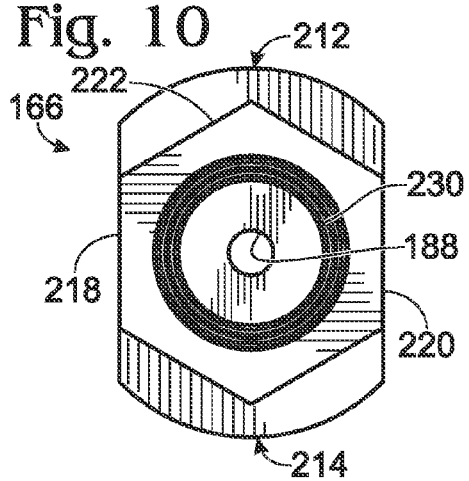
FIG. 10 is an end view of the body portion of FIGS. 7-9, taken generally along line 10-10 of FIG. 9.

FIG. 10 shows an end view of deformable body 166. The structures visible in this view include axial bore 188; threaded regions 212, 214; opposing faces 218, 220; head 222; and internal thread 230; among others.

Figure 11:
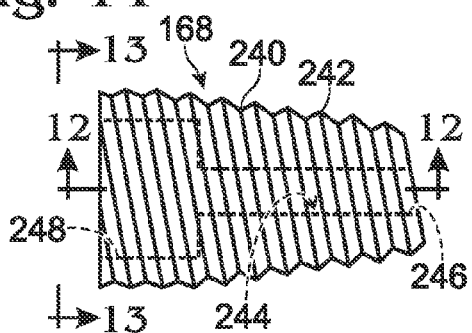
FIG. 11 is a side elevation view of an actuation element (namely, a jackscrew) that assembles with the body portion of FIGS. 7-9 to provide the bendable anchor element of the connector device of FIG. 5.
Figure 12:
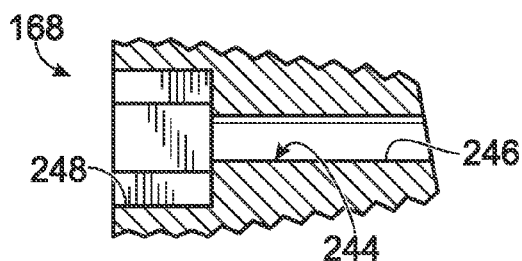
FIG. 12 is a sectional view of the actuation element of FIG. 11, taken generally along line 12-12 of FIG. 11.
Figure 13:
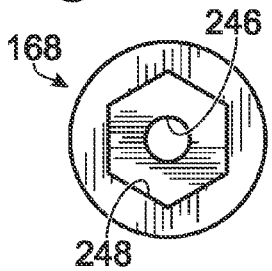
FIG. 13 is an end view of the actuation element of FIG. 11, taken generally along line 13-13 of FIG. 11.

FIGS. 11-13 show respective side, sectional, and end views of actuation element 168. The actuation element may include a cylindrical or tapered (e.g., frustoconical) body 240, also termed a root portion, with an external thread 242 formed thereon. The external thread may be sized and shaped for threaded engagement with the internal thread of the deformable body (e.g., see FIG. 9). The actuation element may be cannulated, defining an axial passage 244 that extends through the actuation element. The axial passage may include a distal section 246 sized to receive the bridge member, and a proximal socket 248 (e.g., a polygonal socket) of greater diameter for receiving a driver that turns the actuation element.

Example 2

Exemplary Method of Connecting Bone Members

This example describes an exemplary method of connecting bone members; see FIGS. 14-20. The method is illustrated using connector device 140 (see Example 1). However, the method may be performed using any suitable connector device such as any of the other connector devices shown and/or described in the present teachings.

Figure 14:
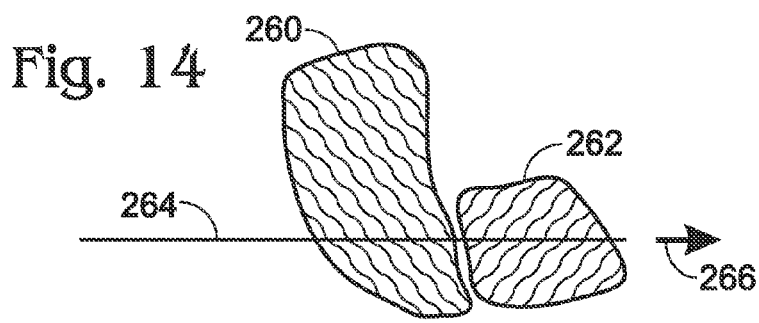
FIG. 14 is a sectional view of a scaphoid bone and a lunate bone taken during performance of an exemplary method of connecting bone members, after placement of a guide member, in the form of a thin guide wire, through the scaphoid and lunate bones, in accordance with aspects of the present teachings.

FIG. 14 shows an exemplary pair of bones, a scaphoid bone 260 and a lunate bone 262, to be connected by performance of an exemplary method of connecting bone members. These carpal bones may be selected for mechanical connection with a connector device due to any suitable indication, such as a fracture and/or a connective tissue injury (e.g., an SLIL injury-see Introduction), among others.

A path for placement of a connector device may be selected using an elongate guide member 264 (e.g., a guide wire) introduced into and/or through bones 260, 262. The guide wire may be introduced first into the scaphoid bone and then into the lunate bone, as indicated by an arrow at 266, or may be introduced in the opposing direction. Furthermore, the guide wire (or other guide member) may have a diameter small enough to permit placement of a cannulated bridge member and/or a cannulated anchor(s) over the guide wire (e.g., see below).

Figure 15:
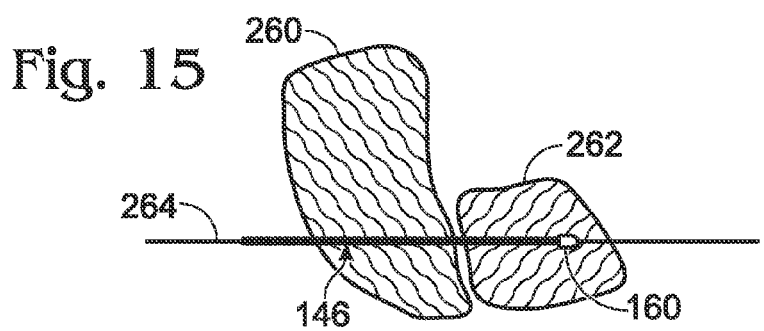
FIG. 15 is another sectional view taken generally as in FIG. 14 during performance of an exemplary method of connecting bone members, after placement of a bridge member, in the form of a connector wire with a head, over the guide wire, in accordance with aspects of the present teachings.

FIG. 15 shows carpal bones 260, 262 after placement of bridge member 146 into the bones. Bridge member 146 may be cannulated, as described above in Example 1, such that the guide wire can extend into and/or through the bridge member as the bridge member is advanced over the guide wire into bone. Head 160 of bridge member 146 may be advanced through the scaphoid bone and into the lunate bone, as shown here, or may be advanced in the opposing direction. Furthermore, head 160 may be advanced through both bones or only into but not through one of the bones (here, lunate bone 262). Advancement of the bridge member may be achieved by drilling a hole over (around and along, e.g., concentric with) the guide wire using a cannulated drill bit, and then placing the bridge member over the guide wire. Alternatively, the bridge member may have a drilling tip (e.g., defined by head 160) such that the bridge member acts as a drill bit that drills a path over the guide wire as the bridge member is rotated by a driver. In other embodiments, the bridge member may be placed into bone without following a path defined by a guide wire, such that the bridge member forms its own path into bone.

Figure 16:
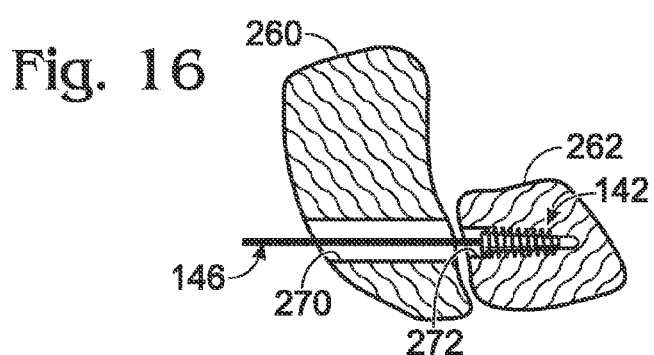
FIG. 16 is yet another sectional view taken generally as in FIG. 14 during performance of an exemplary method of connecting bone members, after placement of a leading anchor through the scaphoid bone and into the lunate bone, and over the bridge member, in accordance with aspects of the present teachings.

FIG. 16 shows carpal bones 260, 262 after placement of leading anchor 142 into lunate bone 262. The leading anchor may be guided by bridge member 146, by placing the leading anchor over the bridge member, such that the stem of the bridge member extends through the cannulation of the leading anchor. The leading anchor may be placed first through scaphoid bone 260 and then into lunate bone 262. (In other embodiments, the leading anchor may be placed into the scaphoid bone from the lunate bone.) Placement of the leading anchor may be facilitated by forming (e.g., drilling) a proximal hole 270 through scaphoid bone 260 and a distal hole 272 extending into lunate bone 262. Proximal hole 270 may be larger in diameter than distal hole 272, and larger in diameter than the maximum diameter of leading anchor 142, to permit the leading anchor to slide translationally through proximal hole 270. Alternatively, or in addition, the leading anchor may be self-drilling such that distal hole 272 (and/or a narrower version of proximal hole 270) may be formed as the leading anchor is rotated into bone. In any event, the leading anchor may be advanced into lunate bone 262 by turning the leading anchor with a driver, such that the leading anchor is secured in the lunate bone through threaded engagement of the external thread of the leading anchor with bone.

Guide wire 264 (see FIGS. 14 and 15) may be removed at any suitable time. For example, the guide wire may be removed, as shown here, after placement of the bridge member into bone over the guide wire (compare FIGS. 15 and 16). Alternatively, the guide wire may be removed and/or shortened (e.g., cut) at any suitable earlier or later time of the procedure. Accordingly, a suitable section of the guide wire extending partially or completely through bones 260, 262 may remain after installation of the connector device is complete.

Figure 17:
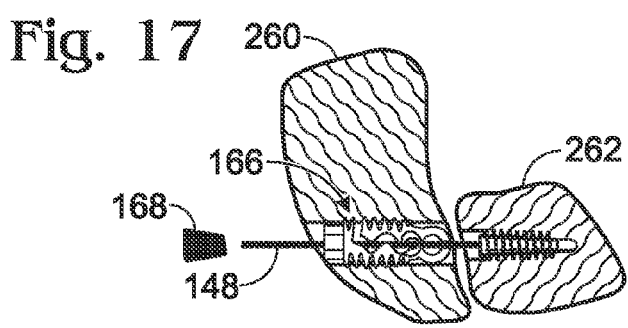
FIG. 17 is still another sectional view taken generally as in FIG. 14 during performance of an exemplary method of connecting bone members, after placement of a body portion of a trailing (bendable) anchor in the scaphoid bone such that the bridge member extends through the body portion and is received by jaws of the body portion, in accordance with aspects of the present teachings.

FIG. 17 shows carpal bones 260, 262 after placement of deformable body 166 of the deformable anchor into the scaphoid bone over the stem (wire 148) of the bridge member. The proximal hole in scaphoid 260 may be smaller than the maximum diameter of the deformable body, such that deformable body is advanced rotationally into the scaphoid bone for threaded engagement with bone. Alternatively, the proximal hole may be sized for advancing the deformable body translationally into the scaphoid bone. In any event, the deformable body may be disposed mostly or completely in the scaphoid bone (see below). Furthermore, the deformable body may be placed into the scaphoid bone already assembled with actuation element 168, but prior to expansion of the deformable body, or the actuation element may be assembled with the deformable body after the deformable body has been placed into bone, as shown here.

Figure 18:
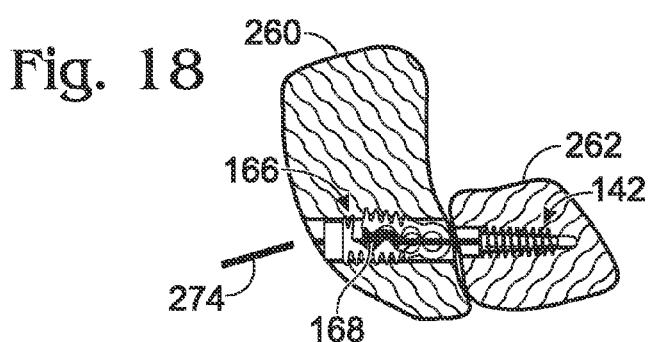
FIG. 18 is yet still another sectional view taken generally as in FIG. 14 during performance of an exemplary method of connecting bone members, after bending the trailing anchor by advancement of an actuation element into the body portion of the trailing anchor and after a protruding section of the bridge member has been removed, in accordance with aspects of the present teachings.

FIG. 18 shows carpal bones 260, 262 after bending deformable body 166 by advancement of actuation element 168 along the deformable body (see below). In addition, a protruding section 274 of the bridge member may be removed by cutting or breaking off the stem of the bridge member. Alternatively, the stem of the bridge member may be cut at any suitable time after placement of the bridge member into bone, for example, prior to placement of leading anchor 142 and/or prior to placement of deformable body 166. In other examples, the stem of the bridge member may have a length, prior to placement into bone, such that the stem does not protrude from the bone after placement and thus does not need to be shortened.

In some embodiments, the stem of the bridge member may be tensioned after placement of the deformable body into bone, but prior to bending the deformable body, to draw the scaphoid and lunate bones together and to urge the leading anchor against the head of the bridge member. However, any suitable amount of "slack" may be left in the stem of the bridge member according to a desired maximum spacing between the scaphoid and lunate bones. In any event, the flexibility of the stem, the tightness of the fit of the stem inside the leading anchor, and/or the length of the stem disposed between the leading anchor and the trailing anchor, among others, may help determine the range of joint motion permitted by the installed connector assembly.

Figure 19:
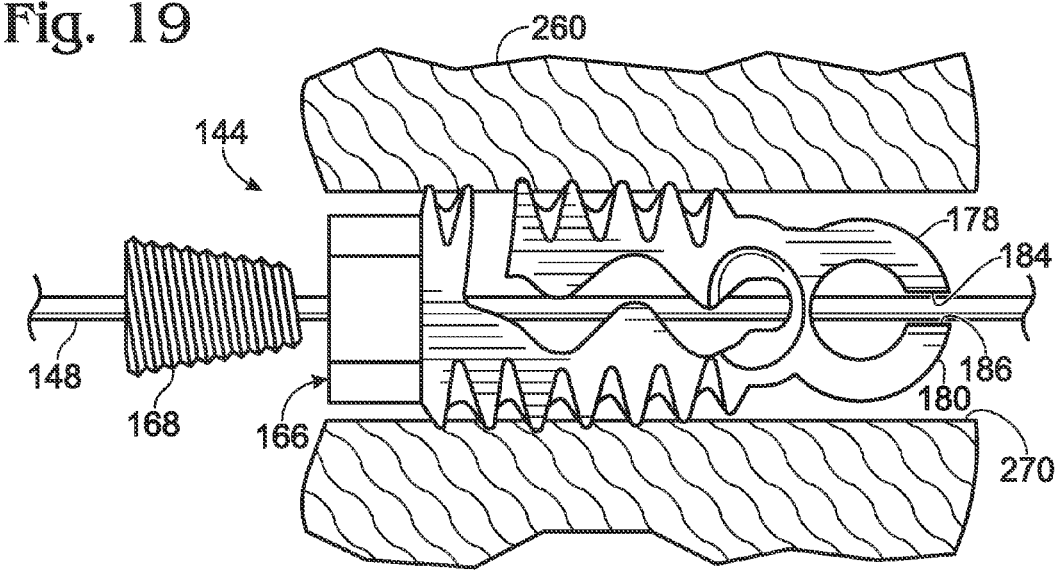
FIG. 19 is a view of selected portions of the connector device of FIG. 5 disposed in bone as in FIG. 17, prior to assembly with the actuation element of the trailing anchor, in accordance with aspects of the present teachings.
Figure 20:
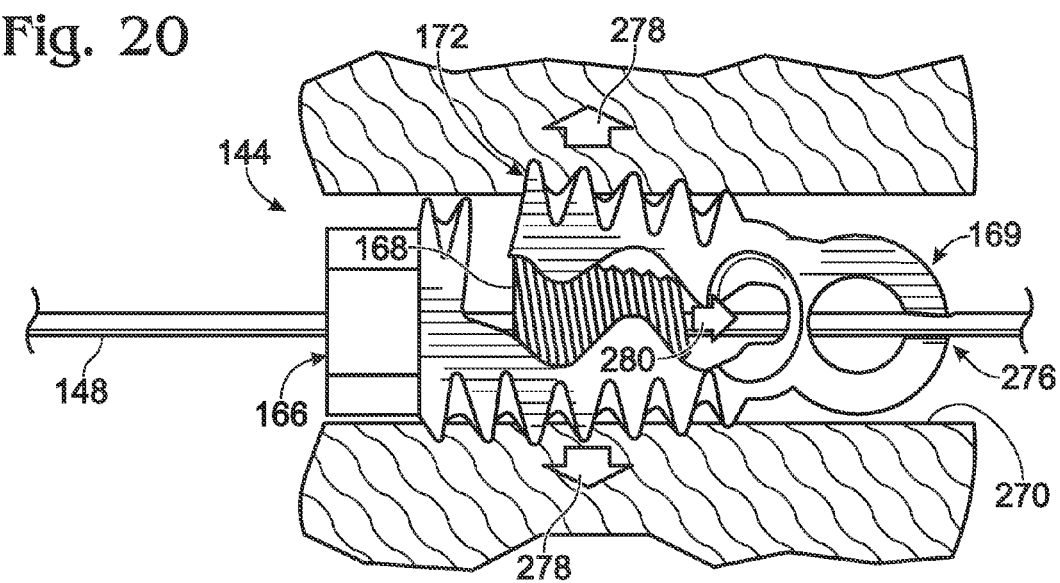
FIG. 20 is a view of selected portions of the connector device of FIG. 5 disposed in bone as in FIG. 18, after advancement of the actuation element into the body portion of the trailing anchor and bending of the body portion such that the trailing anchor grips the bridge member of the connector device, in accordance with aspects of the present teachings.

FIGS. 19 and 20, respectively, show deformable anchor 144 disposed in scaphoid bone 260 before and after assembly of deformable body 166 with actuation element 168. These figures correspond, respectively, to selected portions of FIGS. 17 and 18. In particular, these figures illustrate how coupled expansion and contraction of the body of the deformable anchor may fix the deformable body relative to the bridge member and relative to bone.

FIG. 19 shows deformable body 166 in a pre-gripping configuration. The body may be disposed over the stem (wire 148) of the bridge member such that the stem is received between jaws 178, 180 of the body. The jaws may be in an open configuration such that one or both gripping surfaces 184, 186 of the jaws are spaced from the stem, and/or at least are not engaged tightly with the stem, to permit the deformable body to be repositioned along proximal hole 270 while the stem maintains its longitudinal disposition. The deformable body may be in threaded engagement, shown here, with scaphoid bone 260, or may be received in proximal hole 270 without threaded engagement, depending, for example, upon the diameter selected for the proximal hole.

FIG. 20 shows deformable body 166 gripping stem 148 of the bridge member. Clamp 169 may be actuated to tightly engage and/or crimp the stem, indicated at 276. Expansion region 172 may be expanded outward, away from the central axis of the deformable body, indicated by opposing arrows at 278, by advancement, indicated by an arrow at 280, of actuation element 168, to provide engagement with, increased engagement with, and/or deeper penetration of, the walls of proximal hole 270.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. An implantable orthopedic connector device, comprising:
   an anchor element including an external thread adapted to be disposed in threaded engagement with bone by rotation of the anchor element about an axis and also including jaws, expansion members, and a hinge region, with the hinge region disposed at a position along the axis that is intermediate the expansion members and the jaws;
an actuation element; and
a bridge member,
wherein, with at least a section of the bridge member disposed between the jaws, the actuation element received by the anchor element urges the expansion members apart to bend the anchor element at the hinge region and urging the jaws toward one another and into gripping engagement with the bridge member, thereby fastening the anchor element to the bridge member.

2. The orthopedic connector device of claim 1, wherein the anchor element includes an internal thread, and wherein the actuation element includes an external thread configured to be disposed in threaded engagement with the internal thread of the anchor element.

3. The orthopedic connector device of claim 1, wherein the bridge member includes a rod sized to be received between the jaws.

4. The orthopedic connector device of claim 1, wherein the bridge member includes a wire sized to be received between the jaws.

5. The orthopedic connector device of claim 1, wherein the anchor element is a first anchor element, further comprising a second anchor element including bone-engaging structure and configured to be connected to the first anchor element via the bridge member.

6. The orthopedic connector device of claim 5, wherein the bridge member defines a long axis, and wherein the second anchor element is pivotable relative to the bridge member about the long axis when the anchor elements are connected via the bridge member.

7. The orthopedic connector device of claim 5, wherein the bone-engaging structure of the second anchor element includes an external thread.

8. The orthopedic connector device of claim 1, wherein the jaws, the hinge region, and the expansion members are formed by a same monolithic structure.

9. The orthopedic connector device of claim 1, wherein the anchor element becomes wider when the expansion members are urged apart.

10. The orthopedic connector device of claim 1, wherein the jaws, the hinge region, and the expansion members are formed by a same continuous structure.

11. The orthopedic connector device of claim 1, wherein the hinge region is configured to be deformed when the expansion members are urged apart.

12. An implantable orthopedic connector device, comprising:
a first anchor element and a second anchor element each including bone-engaging structure, the first anchor element defining an axis along which the first anchor element is configured to be advanced into bone and including jaws, expansion members, and a hinge region, with the hinge region disposed at a position along the axis that is intermediate the expansion members and the jaws;
an actuation element; and
a bridge member coupled to the second anchor element,
wherein, with at least a section of the bridge member disposed between the jaws, the actuation element received by the first anchor element urges the expansion members apart to bend the first anchor element at the hinge region and urging the jaws toward one another and into gripping engagement with the bridge member, thereby fastening the first anchor element to the bridge member and connecting the first and second anchor elements to one another via the bridge member.

13. The orthopedic connector device of claim 12, wherein the bridge member is connected pivotably to the second anchor element.

14. The orthopedic connector device of claim 12, wherein the second anchor element defines a passage that extends lengthwise through the second anchor element, and wherein the bridge member extends through the passage and is pivotable with respect to the second anchor element about a long axis defined by the passage.

15. The orthopedic connector device of claim 14, wherein the bridge member includes a stem and a head attached to the stem, and wherein the head is sized to block travel of the head through the passage.

16. The orthopedic connector device of claim 12, wherein the bridge member and the second anchor element are fixed relative to each other.

17. The orthopedic connector device of claim 12, wherein the bone-engaging structure of the second anchor element includes an external thread for threaded engagement with bone.

18. The orthopedic connector device of claim 17, wherein the bone-engaging structure of the first anchor element includes an external thread for threaded engagement with bone.

19. The orthopedic connector device of claim 18, wherein a portion of the external thread of the first anchor element is disposed on each expansion member.

* * * * *